(12) United States Patent
Yoshizane et al.

(10) Patent No.: US 6,440,446 B1
(45) Date of Patent: Aug. 27, 2002

(54) AGENT FOR ANTI-OSTEOPOROSIS

(75) Inventors: Chiyo Yoshizane; Yasushi Nishizaki; Shigeyuki Arai; Masashi Kurimoto, all of Okayama (JP)

(73) Assignee: Kabushiki Kaisha Hayashibara Seibutsu Kagaku Kenkyujo, Okayama (JP)

(*) Notice: Subject to any disclaimer, the term of this patent is extended or adjusted under 35 U.S.C. 154(b) by 0 days.

(21) Appl. No.: 09/293,150

(22) Filed: Apr. 16, 1999

(30) Foreign Application Priority Data

| Apr. 22, 1998 | (JP) | 10-126657 |
| May 20, 1998 | (JP) | 10-153696 |
| May 29, 1998 | (JP) | 10-164468 |
| Jul. 29, 1998 | (JP) | 10-214375 |
| Nov. 6, 1998 | (JP) | 10-316706 |
| Nov. 6, 1998 | (JP) | 10-316709 |

(51) Int. Cl.$^7$ .............. A61F 2/02; A61K 9/48; A61K 9/20
(52) U.S. Cl. .............. 424/423; 424/451; 424/464
(58) Field of Search .............. 424/423, 451, 424/464

(56) References Cited

FOREIGN PATENT DOCUMENTS

EP 0636693 2/1995

OTHER PUBLICATIONS

XP 002112236, Yasushi et al, "Effect of trehalose on the murine osteoporosis model", vol. 137, No. 3, pp. 91–96, 1998.*
XP–002112237, Chemical Abstracts Services, (1998).
XP–002112238, Chemical Abstracts Services, (1996).

* cited by examiner

Primary Examiner—Carlos Azpuru
(74) Attorney, Agent, or Firm—Browdy and Neimark (57) ABSTRACT

An orally or parenterally administrable agent for anti-osteoporosis, comprising trehalose as an effective ingredient and optionally another ingredients, that exerts a satisfactory therapeutic/prophylactic effect on osteoporosis with lesser side effects.

16 Claims, 6 Drawing Sheets

FIG_5

FIG. 6

AGENT FOR ANTI-OSTEOPOROSIS

BACKGROUND OF THE INVENTION

This application claims priority from JP 126657/98 filed Apr. 22, 1998, JP 153696/98 filed May 20, 19998filed 164468/98 filed May 29, 1998, JP 316706/98 filed Nov. 6, 1998, and JP 316709/98 filed Nov. 6, 1998.

1. Field of the Invention

The present invention relates to an agent for anti-osteoporosis, and more particularly to an agent for anti-osteoporosis, comprising trehalose as- an effective ingredient.

2. Description of the Prior Art

Osteoporosis, alias Scalier's disease, is a symptom of the bone where the absolute quantity of bone lowers without qualitative change. In living bodies, osteogenesis by osteoblasts and bone resorption by osteoclasts are continued ceaselessly. osteogenesis is induced by an imbalance between the rates of osteogenesis and bone resorption, caused by some factors, that is inclined to a negative equilibrium side. The major causatives of osteoporosis are classified into environmental- and genetic-factors; the former may be ageing and endocrine diseases such as hyperthyroidism, hypogonadism, Cushing syndrome, etc.; and the latter may be abnormality in an estrogen receptor gene, osteogenesis imperfecta tarda, homocysteinuria, etc. Once osteoporosis is caused, the following occurs successively to make bone porous; the width of cortical bone narrows, the cavity of bone marrow enlarges, and the trabecula of cancellous bone lowers. As osteoporosis progresses, the physical strength of bone lowers, and this makes patients complain frequently about their lumbago and arthralgia and makes their bone broken easily with only a slight shock.

In the treatment of osteoporosis, patients are usually administered with analgesics to relieve pain, and then administered with calcium-metabolism related agents such as preparations of activated vitamin D, calcitonin, estrogen, and protein anabolic hormones. Most of these conventional agents for osteoporosis were hormone preparations which may induce serious side effects; some patients may be forced to cease their administrations before receiving the desired therapeutic effect.

The incidence of osteoporosis is more and more accelerated as ageing. As the graying is just around the corner, it is now greatly need to explore a daily and easily usable agent for anti-osteoporosis that exerts an effective therapeutic/prophylactic effect to live on healthy and to enjoy a worry-free retirement.

SUMMARY OF THE INVENTION

In view of the foregoing, the present object according to the present invention is to provide an agent for anti-osteoporosis that exerts an effective therapeutic/prophylactic effect when administered orally or parenterally.

The present inventors' screening for various substances resulted in a completely unexpected finding that trehalose, a disaccharide, controls the osteogenesis, inclined to a negative equilibrium side, to the normal conditions when administered to mammals and humans, and then exerts a therapeutic/prophylactic effect on osteoporosis with lesser side effects. The present invention solves the above object by providing an orally or parenterally administrable agent for anti-osteoporosis, comprising trehalose as an effective ingredient.

Trehalose is a disaccharide, composed of two glucose molecules bound together at their reducing groups, and is widely distributed in the natural world; it is present in microorganisms, mushrooms, insects, etc. Although the demand of trehalose as a substituent saccharide for sucrose has been increased in the fileds of food products, cosmetics, and pharmaceuticals, the physiological action of trehalose in mammals is not substantially elucidated except for an energy-supplementing action, moisture-imparting action on the skin, and controlling action on fatty acid in the blood.

Trehalose per se is a known compound. The present invention, however, as mentioned above, was made based on a self finding that the trehalose exerts an outstanding anti-osteoporosis in mammals. Thus, the use of trehalose as an orally or parenterally administrable agent for anti-osteoporosis is novel.

DETAILED DESCRIPTION OF THE INVENTION

The present invention relates to an orally or parenterally administrable agent for anti-osteoporosis, comprising trehalose as an effective ingredient. As it is well known, trehalose has three optical isomers with different bonding fashions, i.e., α,α-, α,β- and β,β-trehaloses. Since these compounds exert substantially the same anti-osteoporosis action on mammals and humans, they are advantageously used in the present invention. Thus, in the agent according to the present invention, at least one of these optical isomers can be used in an effective amount in total, and the isomers can be used independently of their preparation and property.

The trehalose usable in the present invention can be prepared by various methods. Leaving out the detailed description of the process for producing trehalose because this invention does not relate to the process in itself, and if considering the production cost of trehalose, methods comprising a step of contacting non-reducing saccharide-forming enzymes and trehalose-releasing enzymes with partial starch hydrolysates, as disclosed in Japanese Patent Kokai Nos. 143,876/95, 213,283/95, 322,883/95, 298,880/

95, 66,187/96, 66,188/96, 336,388/96, and 84,586/96, applied by the same applicant as the present invention, can be satisfactorily used. With these methods, α,α-trehalose is produced from a relatively-low cost of starches as a material in a relatively-high yield. Examples of commercially available products obtained by the methods are "TREHAOSE®", an edible trehalose product containing at least 98% trehalose, on a dry solid basis (d.s.b.), and "TREHASTAR®", a trehalose syrup containing at least 28% trehalose, d.s.b., which are commercialized by Hayashibara Shoji, Inc., Okayama, Japan; and a reagent grade trehalose with a purity of at least 99%, d.s.b., commercialized by Hayashibara Biochemical Laboratories, Inc., Okayama, Japan; α,α-Trehalose can be prepared by using either maltose/trehalose converting enzymes as disclosed in Japanese Patent Kokai Nos. 170,977/95, 263/96, and 149,980/96; or conventionally known maltose- and trehalose-phosphorylases in combination.

To produce trehalose in an α,β-optical isomer, cyclomaltodextrin glucanotransferase and β-galactosidase are allowed to act on a mixture of a partial starch hydrolysate and lactose in this order according to the method disclosed in Japanese Patent Kokai Nos. 144,694/92 and 179,490/92, applied by the present applicant. β,β-Trehalose can be obtained by conventional chemical syntheses. In the present invention, these trehalose isomers should not necessarily be highly purified when orally administered and should not necessarily be separated from other impurities. These optical isomers can be those in an unseparated form or those in a composition form comprising another saccharides produced by-products in the processes used, or can be those in a mixture form comprising another adequate components that do not substantially hinder the anti-osteoporosis action by trehalose on mammals and humans. In the case of injecting the present agent for anti-osteoporosis to humans and animals, pyrogens present in trehalose should preferably be removed before use by using one or more desalting means such as ion exchangers, macroporous resins, activated charcoals, and membrane filters; absorption means; and filtering means.

When administered to mammals and humans, trehalose exerts an action of controlling the balance of osteogenesis and bone absorption to the desired normal conditions; Trehalose acts in such a manner that it maintains the conditions when the balance is in the normal conditions, and acts to recover the balance to the desired conditions when the balance is inclined to a negative equilibrium side as a result of an unsatisfactorily gap between the rates of osteogenesis and bone absorption as found in low-revolutionary osteoporosis, where the osteogenesis rate falls below the normal level to lower the bone content as in geriatric osteoporosis; and found in high-revolutionary osteoporosis, where the bone absorption rate exceeds the normal level to lower the bone content as in hyperparathyroidism. Because of these actions, the administration of trehalose to mammals and humans maintains/promotes the healthy conditions of the bone when the bone is in a good condition, relieves lumbago and arthralgia attendant on osteoporosis in human patients with osteoporosis, increases the bone content, and strengthens the bone not to be broken easily. Thus, the wording "agents for anti-osteoporosis" as referred to in the present invention means pharmaceuticals and food products including beverages, that contain trehalose as an effective ingredient and are taken to treat and/or prevent osteoporosis. The characteristic effects exerted by the present agent for anti-osteoporosis can be confirmed, for example, by the later described test using, as an index, the weight of the femur in ovary-extracted mice.

The agent for anti-osteoporosis according to the present invention can be trehalose alone or compositions comprising trehalose and another ingredients that ease the administration of trehalose. When the compositions are orally administrable ones, they are generally provided in the form of a food product or an orally administrable pharmaceutical composition including foods and fluids for intubation feeding, and more particularly, in the form of a liquid, suspension, emulsion, cream, paste, powder, granule, and another types of solid food products and pharmaceuticals, shaped in a desired form. The present agent in a food-product form is a composition prepared, for example, by using water, alcohols, amylaceous substances, proteins, fibers, saccharides, lipids, vitamins, minerals, flavors, colors, sweeteners, seasonings, flavors, stabilizers, antioxidants, and antiseptics, as well as materials for health foods such as saccharides for promoting the growth of bifid bacteria, powdered milks, milk protein hydrolysates including casein calcium peptides and casein phosphopeptides, lactoferrin, soybean isoflavones, blood meals, bone meals, and powdered corals, which are all generally used in food products as materials and/or ingredients.

These compositions can be those in the form of a food or fluid for intubation feeding. To prepare the present agent in the form of a pharmaceutical, trehalose is processed into a composition by using one or more carriers, excipients/adjuvants, diluents, and stabilizers, and if necessary calcium preparations such as calcium lactate, calcium glycerophosphate, calcium hydrogenphosphate, and calcium L-asparaginate; and another agents such as analgesics, antiphlogistics, activated vitamin D preparations, vitamin K preparations, calcitonin preparations, estrogen preparations, and protein anabolic hormone preparations. Depending on use, the present agent for anti-osteoporosis usually contains trehalose in an amount of at least 0.1 w/w %, and preferably at least one w/w % when used orally.

Explaining the oral use of the present agent for anti-osteoporosis to humans, the present agent exerts a moderate anti-osteoporosis action when administered to humans. Depending on use, in the case of maintaining/promoting the bone conditions and preventing osteoporosis, the present agent is orally administered to humans in the form of a food product. To treat osteoporosis, prevent fracture, and relief lumbago and arthralgia attendant on osteoporosis, the present agent is generally administered to humans in the form of a food product or an orally administrable pharmaceutical such as a liquid, syrup, powder, granule, tablet, or capsule. The daily dose of the present agent is usually about 0.5 to about 100 g/adult/day, and preferably about 1 to about 50 g/adult/day with respect to the amount of trehalose. The present agent can be administered at a dose of 1–5 shots/week very other day.

The present agent for anti-osteoporosis in the form of an injection form is usually prepared by dissolving in water as a base an effective amount of trehalose and one or more ingredients excluding trehalose. The ingredients, which are incorporated into the present agent, include saccharides such as glucose, maltose, fructose, sorbitol, xylitol; electrolytes such as sodium hydroxide, sodium chloride, sodium iodide, sodium acetate, sodium lactate, sodium citrate, sodium monohydrogen-phosphate, potassium dihydrogenphosphate, calcium acetate, calcium lactate, calcium glycerophosphate, calcium gluconate, magnesium sulfate, zinc sulfate, zinc chloride, iron sulfate, ferrous chloride, copper sulfate, and manganese sulfate; amino acids such as L-isoleucine, L-leucine, L-lysine, L-methionine, L-phenylalanine, L-threonine, L-tryptophane, L-valine, L-arginine, L-histidine, glycine, L-alanine, L-cysteine, L-aspartic acid, L-glutamic acid, L-proline, L-serine, and L-thyronine; vitamins such as thiamine chloride, riboflavin monophosphate, pyridoxine hydrochloride, cyanocobalamine, calcium pantothenate, nicotinic acid amide, folic acid, biotin, choline bitartrate, L-ascorbic acid, retinol acetate, tocopherol acetate, and phytonadione; plant and animal lipids such as soybean oil, safflower oil, linseed oil, coconut oil, whale oil, and marine oil; calcium preparations such as calcium lactate, calcium glycerophosphate, calcium hydrogenphosphate, and calcium L-aspartate; and agents such as preparations of activated vitamin D, vitamin K, calcitonin, estrogen, protein anabolic hormones, analgesics, and antiphlogistics.

To prepare the above injectable agents for anti-osteoporosis according to the present invention, trehalose is dissolved in water together with one or more of the above ingredients other than trehalose in an amount that makes the trehalose content 0.1 w/w % or more, and more preferably 1–10 w/w %. The resulting mixtures are sterilized by filtering using membrane filters, etc., injecting aseptically the filtrates into appropriate containers after controlling the osmotic pressure if necessary, and then cap sealing the containers directly or after lyophilizing the contents. The pH of the solutions is preferably adjusted to around neutral pH, and more particularly to pHs of about 6.0 to about 7.5. The solutions can be kept at these pHs by the addition of an adequate amount of acids and/or alkalis or the addition of pharmaceutically-acceptable buffers such as phosphate- and carbonate-buffers.

Explaining the injection use of the present agent for anti-osteoporosis to humans, the present agent exerts an outstanding anti-osteoporosis action without inducing serious side effects when injected. To maintain/promote the health conditions of the bone and to prevent osteoporosis, the present injectable agent, after dissolving in a relatively-small amount of a solution not more than 100 ml, is administered to humans at one shot within one hour by injection, instillation, etc. To relieve lumbago and arthralgia and to prevent fracture, the present injectable agent, after dissolving in a relatively-large amount of a solution not more than 500 ml, is administered to humans at one shot by instillation, etc. In each case, the administration rate should preferably be not higher than 0.5 g/kg body weight/hour with respect to trehalose by weight, and an administration time should preferably be within two hours. The present injectable agent for anti-osteoporosis can be administered to humans, for example, by subcutaneous-, intramuscular-, intraperitoneal-, or intravenous-injection; the intravenous administration is most preferable. Depending on use, the agent is usually administered to humans at a dose of about 0.5 to about 100 g/adult/day, and preferably at about 1 to about 50 g/adult/day with respect to the dose of trehalose.

The following Experiments 1–3 describe the effect and safety of the orally-administrable agent for anti-osteoporosis according to the present invention, and Experiments 4–5 describe the effect and safety of the injectable agent for anti-osteoporosis according to the present invention:

Experiment 1

Animal Experiment

According to what is done conventionally, female ddY mice, 4-week-old, which had been grouped into 34 heads/group based on their body weight, were anesthetized with sodium pentobarbital, and extracted their ovaries. From the next day, the mice were orally administered with "TREHAOSE®", a crystalline trehalose powder containing at least 98% trehalose, d.s.b., commercialized by Hayashibara Shoji, Inc, Okayama, Japan, which had been dissolved in distilled water, at a dose of 0.01, 0.1 or 1 g/kg body weight per shot once every day, five shots in a week. Four weeks after completion of the administration, the mice were weighed, sacrificed in the usual manner, and extracted their both sides of femurs, followed by drying the femurs under heating conditions at 110° C. overnight and weighing the dried contents. The feed used was a low-calcium feed for ease of making the difference of the bone content.

In parallel, the following control groups were provided and treated similarly as the group with trehalose: As control 1, a group in which mice were administered with the same amount of distilled water as the aqueous trehalose solution in place of the trehalose solution; as control 2, a group in which mice were administered with estradiol, as a therapeutic agent for osteoporosis, dissolved in the same amount of distilled water as the aqueous trehalose solution in place of the trehalose solution, at a dose of one mg/kg body weight/shot, two times a week; and as control 3, a group in which mice, which were received with a laparotomy pseudo-operation and not extracted their ovaries, were administered with the same amount of distilled water as the aqueous trehalose solution in place of the trehalose solution. The dry weight of femurs of the mice with trehalose and that in controls 1 to 3 were tabulated in Table 1. Some of the mice administered with trehalose at a dose of 0.1 g/kg body weight/shot, and the mice in controls 1 and 3 as groups with no trehalose were extracted their tibias, followed by observing the tibias microscopically. The specimens for microscopic observation were prepared in the usual manner by immobilizing the extracted tibias with formalin solution, washed with water, delimed, split along with the long axis, and treated with protease K to remove bone marrow cells. The specimens of tibias were observed by a relatively-low vacuum electron-microscope under 24 magnifications, and photographed. The data are respectively in FIGS. 1 to 3. In these figures, white parts are the trabecula of cancellous bone. The osteoporosis occurred in the mice extracted their ovaries is called oophorectomized osteoporosis and is an excellent model for postmenopausal osteoporosis as a geriatric osteoporosis.

TABLE 1

| Test sample | Body weight when tibia was enucleated (g) | Dry weight of extracted tibia (mg) | Dry weight of extracted tibia Body weight (mg/g) | Remark |
| --- | --- | --- | --- | --- |
| Distilled water | 32.2 ± 2.0 | 91.1 ± 6.8 | 2.921 ± 0.202 | Control 3 |
| Distilled water | 31.7 ± 2.0 | 83.1 ± 5.8 | 2.625 ± 0.168 | Control 1 |
| Trehalose | 31.7 ± 2.2 | 83.6 ± 7.0 | 2.643 ± 0.195 | Present invention |

TABLE 1-continued

| Test sample | Body weight when tibia was enucleated (g) | Dry weight of extracted tibia (mg) | Dry weight of extracted tibia Body weight (mg/g) | Remark |
|---|---|---|---|---|
| (0.01 g/kg body weight) Trehalose | 31.3 ± 2.4 | 85.0 ± 5.2 | 2.723 ± 0.163 | Present invention |
| (0.1 g/kg body weight) Trehalose | 32.0 ± 2.1 | 88.4 ± 6.4 | 2.762 ± 0.172 | Present invention |
| (1 g/kg body weight) Estradiol | 31.8 ± 2.0 | 119.9 ± 7.5 | 3.520 ± 0.240 | Control 2 |

Figure 1:
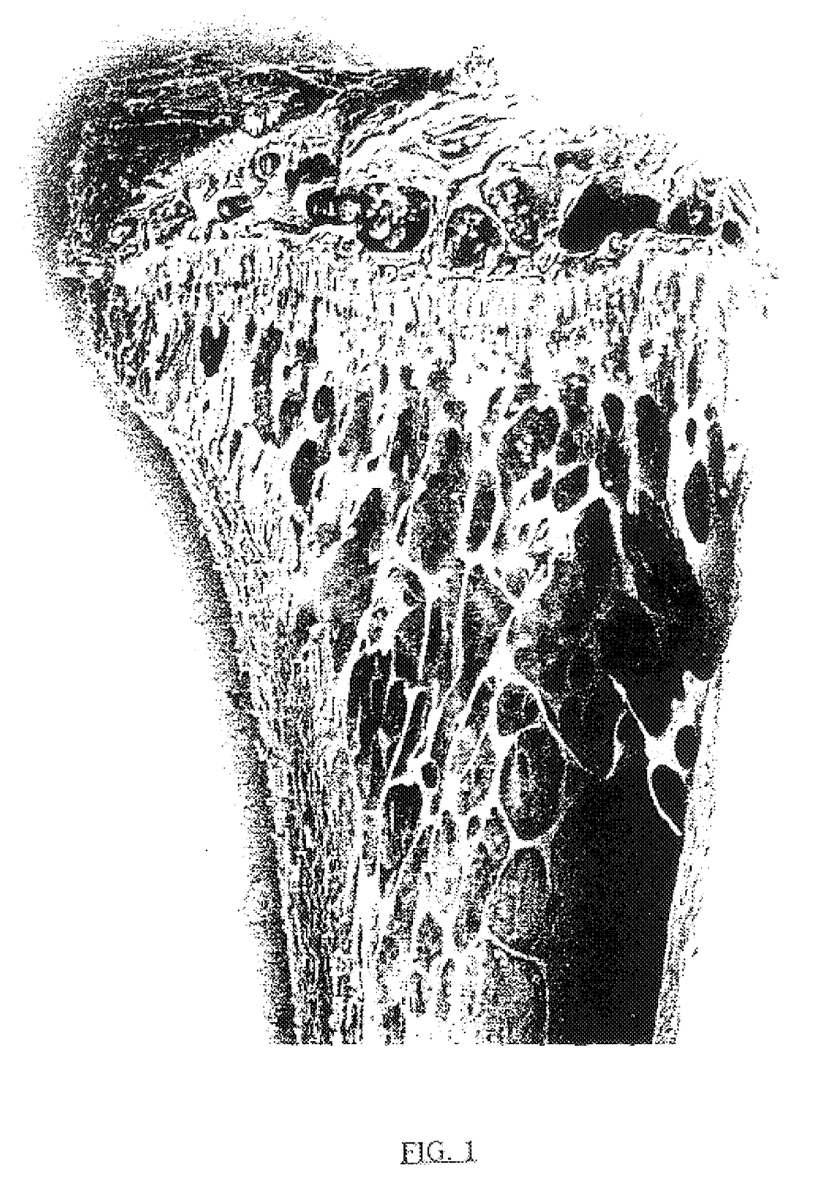
FIG. 1 is an intermediate tone image of a photograph (×24), displayed on a display, of the tibia of a mouse in an ovary-removed mouse group with trehalose, photographed under a low-vacuum scanning electron microscope.
Figure 2:
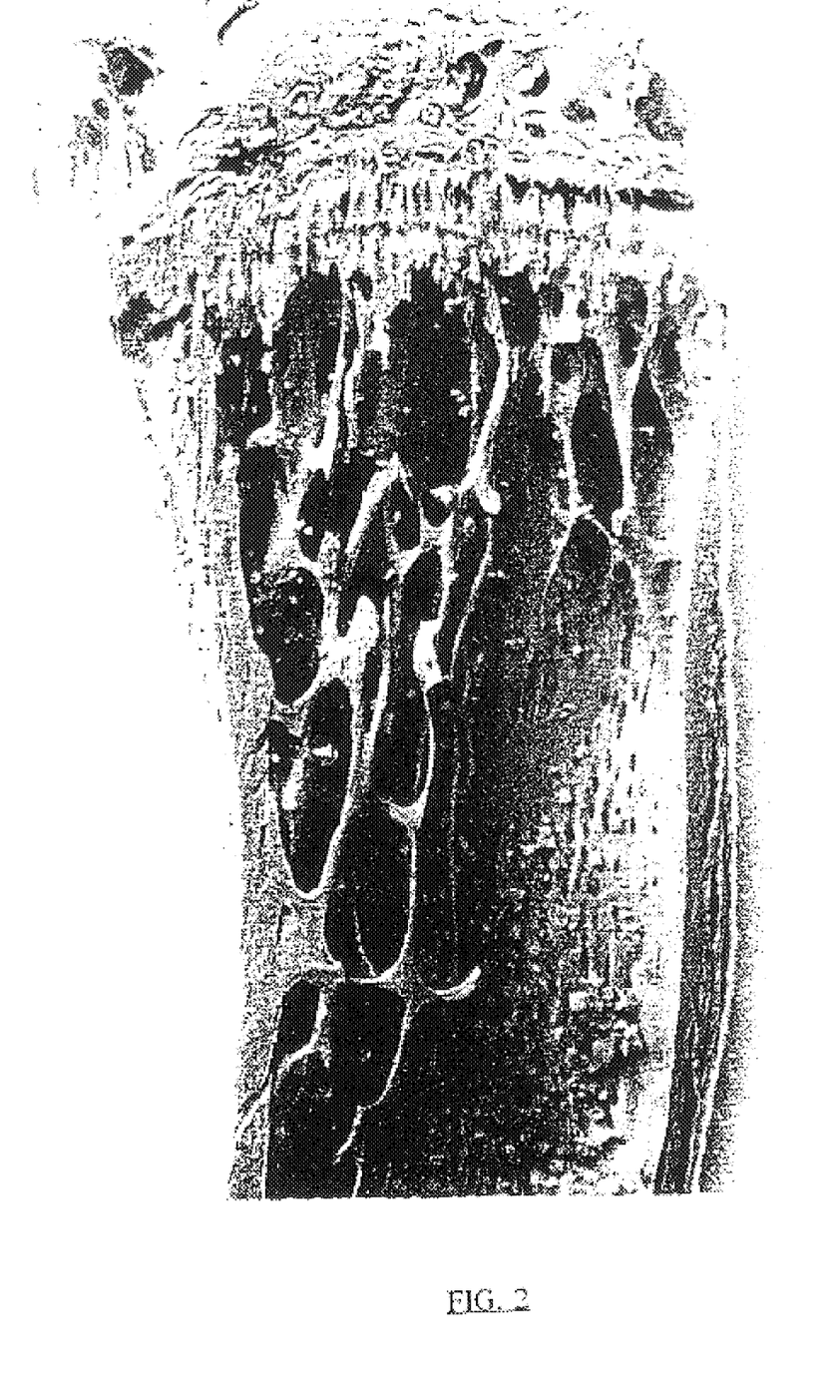
FIG. 2 is an intermediate tone image of a photograph (×24), displayed on a display, of the tibia of a mouse in an ovary-removed mouse group with no trehalose, photographed under a low-vacuum scanning electron microscope.
Figure 3:
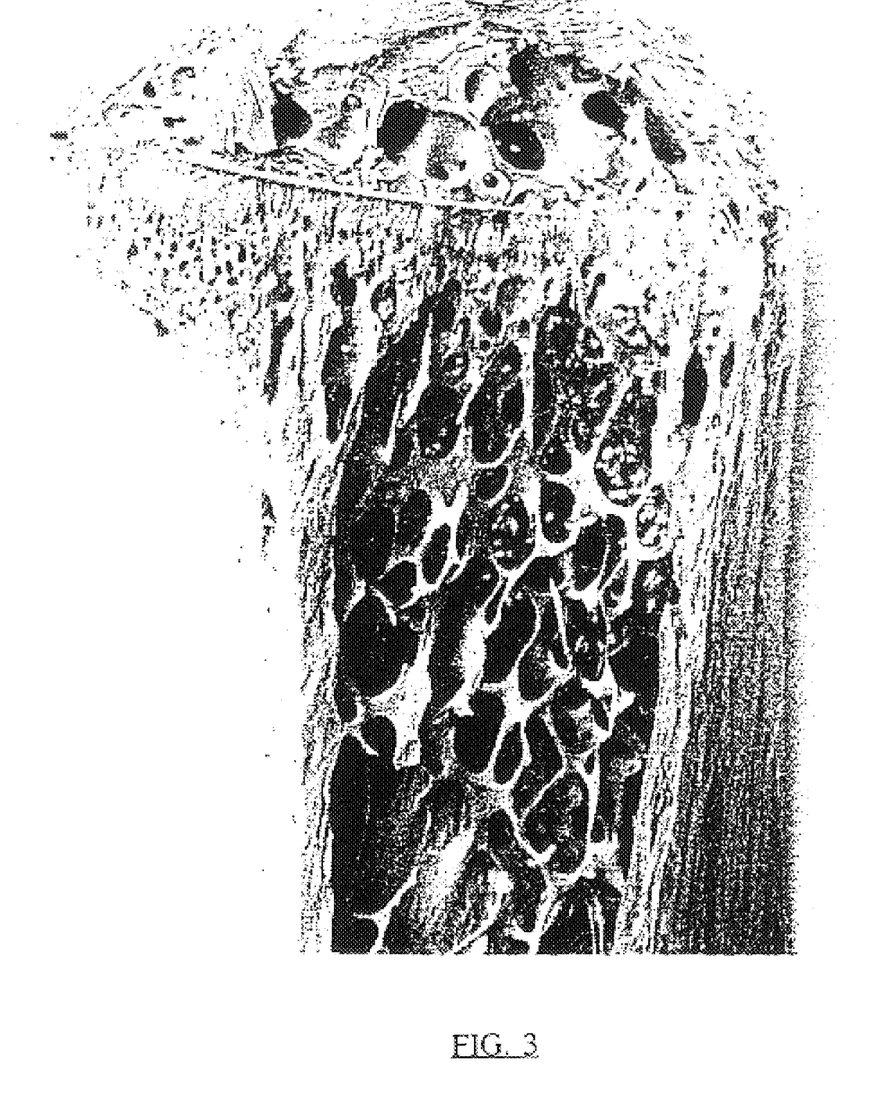
FIG. 3 is an intermediate tone image of a photograph (×24), displayed on a display, of the tibia of a mouse in an ovary-non-removed mouse group with no trehalose, photographed under a low-vacuum scanning electron microscope.

The data in Table 1 shows that, when taken orally by mammals, trehalose significantly inhibits the lowering of the bone content attendant on osteoporosis, although the effect is not so prompt as estradiol. The inhibitory effect on the lowering of the bone content was found at a dose of about 0.1 g/kg body weight/shot of trehalose, and the effect was more increased at a dose of one g/kg body weight/shot. The action of trehalose can be understood from the photographs of FIGS. 1 to 3. Comparing the tibias in FIGS. 1 and 2 while regarding FIG. 3 as the normal one, the tibia in control 1, as shown in from the middle part to the lower part in. FIG. 2, the reduction of the trabecula in cancellous bone and the expansion of the cavity of marrow, typically observed in osteoporosis, were clearly found, and the bone was physically weakened. While the tibia in the group with trehalose, as shown in FIG. 1, the reduction of trabecula in cancellous bone and the expansion of the cavity of marrow were clearly inhibited, and the bone was physically strengthened. No abnormality induced by the administration of trehalose was found after careful observation throughout the experiment. As data is not shown, a group, where mice were administered with sucrose in place of trehalose, was provided and tested similarly as the mice with trehalose. As a result, no significant difference was found as compared with the control group where mice were extracted their ovaries and administered with distilled water.

Similarly as above, the tibias were extracted from some mice, excluding the aforesaid mice which had been extracted their tibias, in the group with trehalose at a dose of 0.1 g/kg body weight/shot, and in the groups 1 and 3. From each tibia, bone marrow cells were collected in the usual manner and suspended in α-MEM medium, supplemented with 10 v/v % fetal calf serum, to give a cell density of $1.5 \times 10^6$ cells/ml. The resulting cell suspensions were respectively placed in 24-well plates in a volume of 0.5 ml/well. To each well was added 0.25 ml/well of a cell suspension with a cell density of $4 \times 10^4$ cells/ml of osteoblast-like cells suspended in a fresh preparation of the same medium as above. A solution of $4 \times 10^9$M 1α, 25-dihydroxy vitamin $D_3$, dissolved in a fresh preparation of the same medium as above, was added to each well in a volume. of 0.25 ml/well. The resulting cell suspension mixtures were incubated in a 5 v/v % $CO_2$ incubator at 37° C. for six days while replacing the media with a fresh preparation of α-MEM medium containing $1 \times 10^9$M 1α, 25-dihydroxy vitamin $D_3$ and 10 v/v % fetal calf serum.

After completion of the culture, the supernatants were removed, and the cells in each well were fixed with formalin, and treated in the usual manner with "NAPHTHOL AS-MS PHOSPHATE" and "RED VIOLET LB SALT", which are commercialized by Sigma Chemical Company, ST. Louis, Mo., USA, to stain the cells having a tartaric-acid-resistant-acid-phosphatase activity. The differentiated osteoclasts have a tartaric-acid-resistant-acid-phosphatase activity and a feature of multinucleation. After staining, each well was microscopically observed to count multinucleated cells for determining the number of osteoclasts. As a result, the osteoclasts in the well of control 1 was at least 3-times higher than that of control 2, while the number of osteoclasts in the group with trehalose was about 2-times higher than that of control 2. This shows that trehalose has an activity of inhibiting the differentiation of osteoclasts. There found good correlations between the lowering of the bone content attendant on osteoporosis and the differentiation induction of osteoclasts in the above experimental animals of control 1, and also between the inhibition of the lowering of the bone content and the differentiation induction inhibition of osteoclasts in the group with trehalose.

These data of Experiment 1 indicate that trehalose controls the osteogenesis, inclined to a negative equilibrium side, to the normal conditions and exerts a moderate anti-osteoporosis action, and that the action by trehalose to inhibit the differentiation of osteoclasts relates to the above action.

Experiment 2

Clinical Test

Thirty-four volunteers, consisting of 17 males and females respectively, 60 to 72 years old, who were suffering from lumbago and arthralgia attendant on geriatric osteoporosis and post-traumatic osteoporosis, were divided into two groups consisting of nearly the same numbers of both sexes, and allowed to intake either the present agent for anti-osteoporosis prepared by the method in the later described Example 5, or a placebo similarly as in Example 5 except for replacing trehalose with sucrose at a dose of five tablets/shot every after meal over one month. Throughout the experiment, medical technologists conducted the experiment and asked the volunteers their conditions at prescribed times. After completion of the experiment, the effects of the samples tested were graded into four ranks; "very efficacious", "slightly efficacious", "unchanged", and "worsened" based on the results of the inquiries. The efficacy (%) is expressed as a percentage of the total number of volunteers, who answered "very efficacious" and "slightly efficacious", to the total number of volunteers in each group. The results are in

TABLE 2

| | Test sample | |
|---|---|---|
| Judgement | Agent for Anti osteoporosis according to the present invention | Placebo |
| Very efficacious | 2 | 0 |
| Slightly efficacious | 5 | 1 |

TABLE 2-continued

| | Test sample | |
|---|---|---|
| Judgement | Agent for Anti osteoporosis according to the present invention | Placebo |
| Unchanged | 10 | 15 |
| Worsened | 0 | 1 |
| Efficacy (%) | 41 | 6 |

The data in Table 2 shows that the present agent for anti-osteoporosis is effective on relieving lumbago and arthralgia attendant on osteoporosis; The efficacy of the group with the placebo was lower than 10%, while the group with the present agent was as high as over 40%. There found no volunteer who complained about his or her mental and physical conditions after receiving the present agent, while most of the volunteers answered that they slept well, relaxed comfortably, defecated regularly, and that the previous defectiveness on working and walking were reduced. These results indicate that the present agent for anti-osteoporosis exerts a moderate anti-osteoporosis action.

Experiment 3
Acute Toxicity test

An adequate amount of "TREHAOSE®", a crystalline trehalose powder having at least 98% of trehalose, d.s.b., commercialized by Hayashibara Shoji, Inc., Okayama, Japan, was dissolved in physiological saline containing 5 w/w % gum arabic, and the solution was sterilized in the usual manner. The sterilized solution was injected intraperitoneally or orally administered using a gastric tube to ddY mice, 20–25 g weight, in a group of 10 heads, followed by the observation for seven days. As a result, independently of the administration routes, no mouse died even administered with the maximum dose, 15 g/kg body weight. The data shows that the present agent for anti-osteoporosis can be daily administered to mammals and humans with lesser side effects.

Experiment 4
Animal Experiment

An injection containing 10 w/w % trehalose, obtained by the later described Example 7, was diluted with a phosphate buffered saline, which had been filtered with a membrane filter having a pore size of 0.22 μm (hereinafter abbreviated as "PBS") into a 0.1 w/w % or 1 w/w % trehalose solution. These solutions and the above injection were used for test samples. According to what is done conventionally, female ddY mice, 4-week-old, which had been grouped into 34 heads/group based on their body weight, were anesthetized with sodium pentobarbital, and extracted their ovaries. From the next day, the mice were injected from their tail veins with any one of the test samples at a dose of 5 ml/kg body weight/shot, once every day and five times a week. Four weeks after completion of the administration, the mice were weighed, sacrificed in the usual manner, and extracted their both sides of femurs, followed by drying the femurs under heating conditions at 110° C. overnight and weighing the dried contents. The feed used was a low-calcium feed for ease of making the difference of the bone content.

Figure 5:
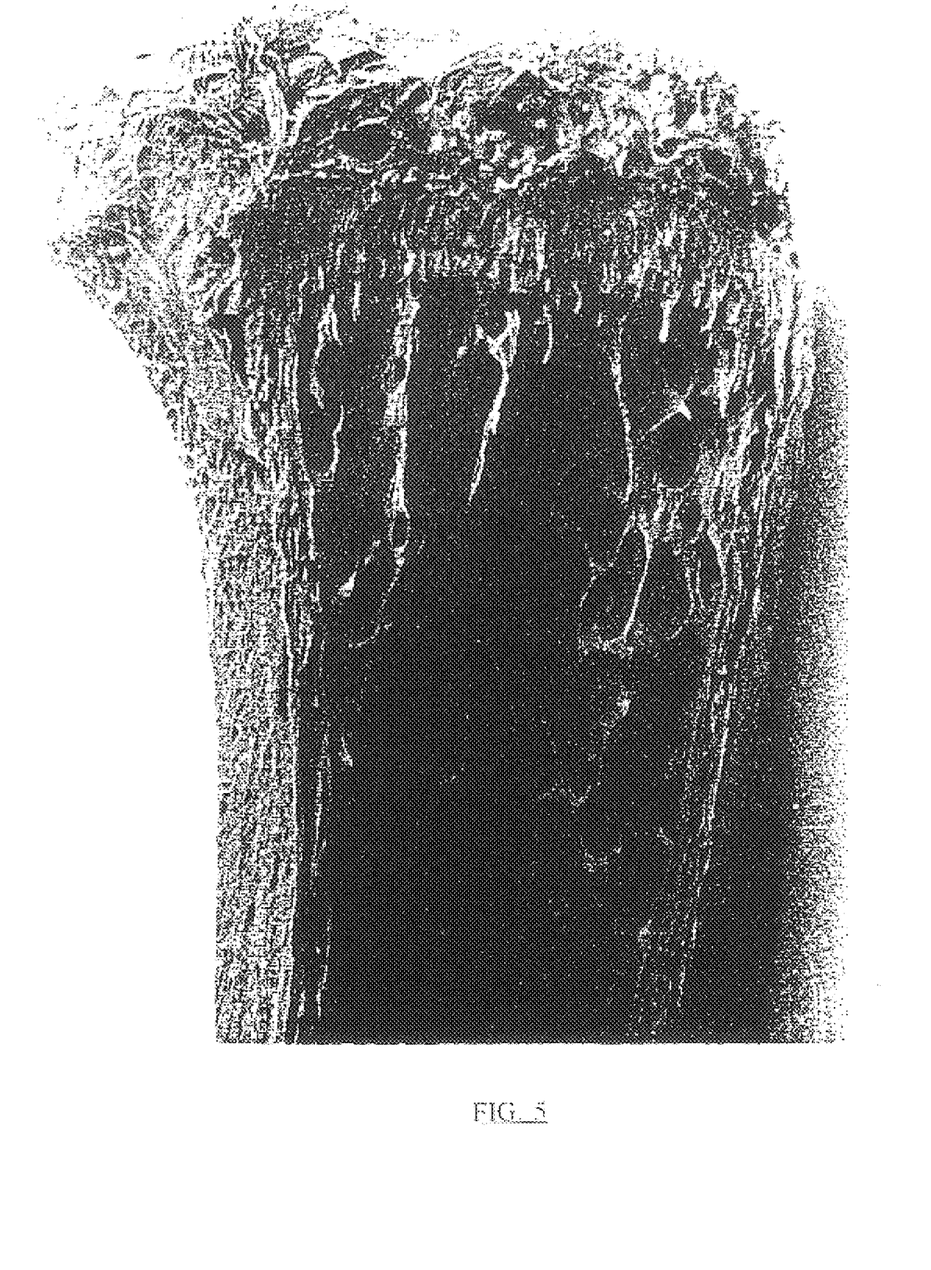
FIG. 5 is an intermediate tone image of a photograph (×24), displayed on a display, of the tibia of a mouse in an ovary-removed mouse group with no trehalose, photographed under a low-vacuum scanning electron microscope.
Figure 6:
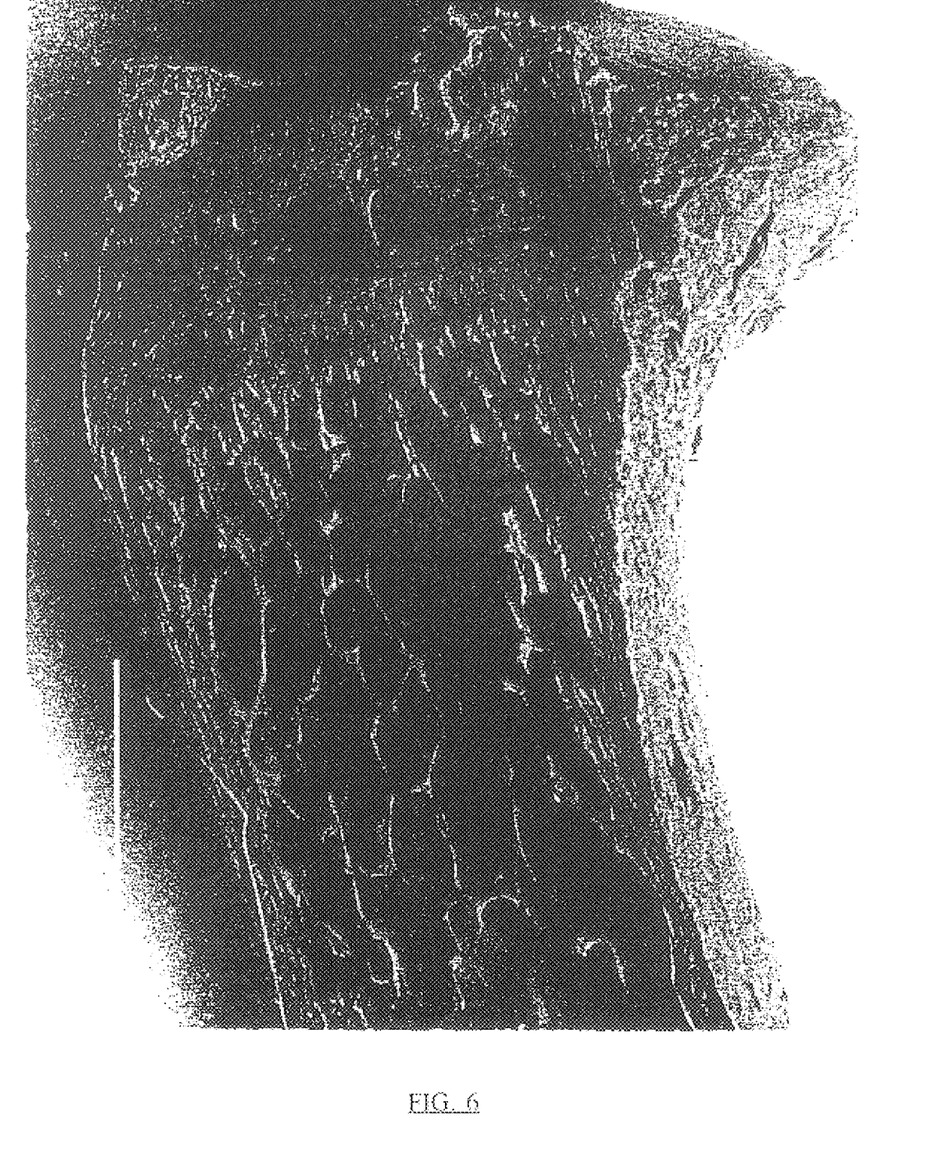
FIG. 6 is an intermediate tone image of a photograph (×24), displayed on a display, of the tibia of a mouse in an ovary-non-removed mouse group with no trehalose, photographed under a low-vacuum scanning electron microscope.

In parallel, the following control groups were provided and treated similarly as the group with trehalose: As control 1, a group in which mice were administered with the same amount of PBS as the test samples in place of them; and as control 2, a group in which mice, that were received with a laparotomy pseudo-operation and were not extracted their ovaries, were administered with the same amount of PBS as the test samples in place of them. The dry weight of femurs of the mice with test samples and that in controls 1 and 2 were tabulated in Table 3. Some of the mice administered with trehalose using one w/w t trehalose solution, and the mice in controls 1 and 2 as non-trehalose administration groups were extracted their tibias, followed by observing the tibias microscopically. The specimens for microscopic observation were prepared in the usual manner by immobilizing the extracted tibias with formalin solution, washed with water, delimed, split along with the long axis, and treated with protease K to remove bone marrow cells. The specimens of tibias were observed by a relatively-low vacuum electron-microscope under 24 magnifications, and photographed. The data are respectively in FIGS. 4 to 6. In these figures, white parts are the trabecula of cancellous bone. The osteoporosis occurred in mice extracted their ovaries is called oophorectomized osteoporosis and is an excellent model for postmenopausal osteoporosis as a geriatric osteoporosis.

TABLE 3

| Test sample | Body weight when tibia was enucleated (g) | Dry weight of extracted tibia (mg) | Dry weight of extracted tibia Body weight (mg/g) | Remark |
|---|---|---|---|---|
| PBS | 32.3 ± 2.1 | 90.9 ± 6.7 | 2.814 ± 0.207 | Control 2 |
| PBS | 31.6 ± 1.9 | 82.9 ± 5.7 | 2.623 ± 0.180 | Control 1 |
| Test sample (0.1% trehalose) | 31.9 ± 2.0 | 84.2 ± 6.9 | 2.639 ± 0.213 | Present invention |
| Test sample (1% trehalose) | 32.0 ± 2.2 | 86.9 ± 6.1 | 2.716 ± 0.191 | Present invention |
| Test sample (10% trehalose) | 32.3 ± 2.1 | 89.7 ± 5.5 | 2.777 ± 0.170 | Present invention |

Figure 4:
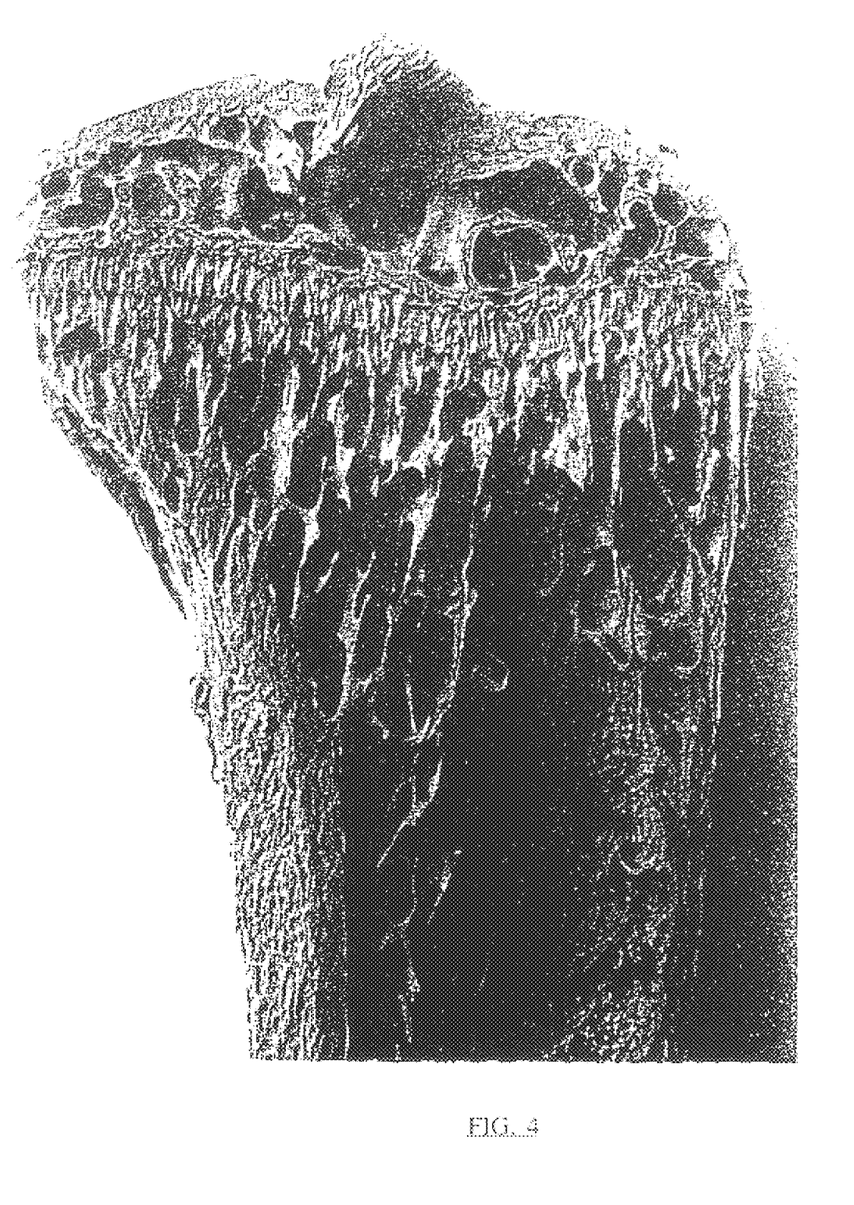
FIG. 4 is an intermediate tone image of a photograph (×24), displayed on a display, of the tibia of a mouse in an ovary-removed mouse group with trehalose, photographed under a low-vacuum scanning electron microscope.

The data in Table 3 shows that, when intravenously administered to mammals, trehalose significantly inhibits the lowering of the bone content attendant on osteoporosis. The inhibitory effect on the lowering of bone content was found at a dose of about 5 ml/kg body weight/shot of 1 w/w % trehalose, and the effect was more increased at the same dose of 10 w/w % trehalose. The action of trehalose can be understood from the photographs of FIGS. 4 to 6. Comparing the tibias in FIGS. 4 and 5 while regarding FIG. 6 as the normal one, the tibia in control 1, as shown in from the middle part to the lower part of FIG. 5, the reduction of the trabecula in cancellous bone and the expansion of the cavity of marrow, typically observed in osteoporosis, were clearly found, and the bone was physically weakened. While the tibia in the group with trehalose, as shown in FIG. 4, the reduction of the trabecula in cancellous bone and the expansion of the cavity of marrow were clearly inhibited, and the bone was physically strengthened. No abnormality induced by the administration of trehalose was found after careful observation throughout the experiment. As data is not shown, groups, where mice were administered with glucose, maltose, sorbitol, or xylitol in place of trehalose, were respectively provided and tested similarly as the mice with trehalose. As a result, no significant difference was found as compared with the control groups where mice were extracted their ovaries and administered with PBS intraperitoneally.

Similarly as above, the tibias were extracted from some mice, excluding the aforesaid mice which had been extracted their tibias, in the group with 10% trehalose solution at a dose of about 5 ml/kg body weight/shot, and in the groups 1 and 3. From each tibia, bone marrow cells were collected in the usual manner and suspended in α-MEM medium, supplemented with 10 v/v % fetal calf serum, to give a cell density of $1.5 \times 10^6$ cells/ml. The resulting cell suspensions were respectively placed in 24-well plates in a volume of 0.5 ml/well. To each well was added 0.25 ml/well of a cell suspension with a cell density of $4 \times 10^4$ cells/ml of osteoblast-like cells suspended in a fresh preparation of the same medium as above. A solution of $4 \times 10^9 M$ 1α, 25-dihydroxy vitamin $D_3$, dissolved in a fresh preparation of the same medium as above, was added to each well in a volume of 0.25 ml/well. The resulting cell suspension mixtures were incubated in a 5 v/v % $CO_2$ incubator at 37° C. for six days while replacing the media with a fresh preparation of α-MEM medium containing $1 \times 10^9 M$ 1α, 25-dihydroxy vitamin $D_3$ and 10 v/v % fetal calf serum.

After completion of the culture, the supernatants were removed, and the cells in each well were fixed with formalin, and treated in the usual manner with "NAPHTHOL AS-MS PHOSPHATE" and "RED VIOLET LB", which are commercialized by Sigma Chemical Company, ST. Louis, Mo., USA, to stain the cells with a tartaric-acid-resistant-acid-phosphatase activity. The differentiated osteoclasts have a tartaric-acid-resistant-acid-phosphatase activity and a feature of multinucleation. After staining, each well was microscopically observed to count multinucleated cells for determining the number of osteoclasts. As a result, the osteoclasts in the well of control 1 was at least 3-times higher than that of control 2, while the number of osteoclasts in the group with trehalose was about 2-times higher than that of control 2. This shows that trehalose has an activity of inhibiting the differentiation of osteoclasts. There found good correlations between the lowering of the bone content attendant on osteoporosis and the differentiation induction of osteoclasts in the above experimental animals of control 1, and also between the inhibition of the lowering of the bone content and the differentiation induction inhibition of osteoclasts in the group with trehalose.

These data of Experiment 1 indicate that trehalose controls osteogenesis, inclined to a negative equilibrium side, to the normal conditions to exert a moderate anti-osteoporosis action, and that the differentiation induction inhibitory action by trehalose on osteoclasts relates to the above action.

Experiment 5

Acute Toxicity Test

According to what is done conventionally, male rabbits of *Oryctolagus cuniculus* (a Japanese white rabbit), about three kilograms each, in a group of five heads, were placed in cases for fixing them, administered continuously from their auricular veins with any one of the injections, obtained by the methods in Examples 7 and 8, intact or after dissolving in an adequate amount of distilled water for injection, at an administration rate of 5 ml/kg body weight/hour and a different administration period for each group up to the maximum period of six hours, and then observed their conditions for seven days. As a result, no mouse died even at the maximum possible dose of 3 g/kg body weight of trehalose. The data shows that the present agent for anti-osteoporosis is administered to humans and animals with lesser side effects.

The following Examples 1–6 describe the preferred embodiments of the orally-administrable agents according to the present invention, and the following Examples 7–8 describe the preferred embodiments of the injectable agents according to the present invention:

Example 1

Health Food

According to what is done conventionally, after subjecting reducing sugars contained in potato to autolysis under storing conditions at 20° C. and at a relative humidity of 85% for two weeks, the potato was washed with water, pealed, graded, and sliced with a centrifugal slicer into slices, 1.5 mm in thickness.

The slices were washed with water to remove starch on their surfaces, drained, and fried at 170° C. for about five minutes, followed by removing oil. Using a salter, a powdery seasoning containing seven parts by weight of salt, three parts by weight of "TREHAOSE®", a crystalline trehalose powder having at least 98% of trehalose, d.s.b., commercialized by Hayashibara Shoji, Inc., Okayama, Japan, and an adequate amount of a flavor was spayed over the above fried potato which was then transferred to a machine for weighing, injected, and packaged to obtain a refreshment containing trehalose.

The product, having a satisfactory flavor and taste, is useful as a health food for maintaining/promoting the health conditions of the bone.

Example 2

Health Food

To 25 parts by weight of well-kneaded butter were successively added 18 parts by weight of "TREHAOSE®", a crystalline trehalose powder containing at least 98% of trehalose, d.s.b., commercialized by Hayashibara Shoji, Inc, Okayama, Japan, and 10 parts by weight of eggs, and the mixture was stirred into a cream. Forty-seven parts by weight of a soft flour was added to the cream, and the mixture was well kneaded, rolled with a cloth, and allowed to stand for 20 min. The resulting dough was shaped into a rod, 3 cm in diameter, rolled with a paraffine paper, and allowed to stand at 4° C. for two hours. Thereafter, the dough was cut into rings, 5 mm thick, and then placed on a plain plate with oil, grilled at 170° C. for 10 min, coated with "TREHASTAR®", a trehalose syrup containing at least 28% trehalose, d.s.b., commercialized by Hayashibara Shoji, Inc., Okayama, Japan, and further grilled at the same time for 10 min to obtain an ice-box cookie.

The product, having a satisfactory flavor and taste, is useful as a health food for maintaining/promoting the health conditions of the bone.

Example 3

Health Food

Seven parts by weight of a freeze-dried tea extract and three parts by weight of "TREHASTAR®", a trehalose syrup containing at least 28% trehalose, d.s.b., commercialized by Hayashibara Shoji, Inc., Okayama, Japan, were dissolved in an appropriate amount of water. The resulting solution was in the usual manner fermented and sprayed with 90 parts by weight of a dried tea-leaf. According to what is done conventionally, the tea leaf was sieved, cut, dried, and subjected to a separator to remove impurities, followed by packing two gram aliquots of the contents with a Japanese paper into tea bags containing trehalose.

Before drinking, the product is soaked in a 180 ml cold water for about 10 minutes or in a 180 ml water heated to 90–100° C. for about two minutes. The product, having a satisfactory flavor and taste, is useful as a health food for maintaining/promoting the health conditions of the bone.

Example 4
Health Food 2.7 parts by weight of "TETRUP®", a maltotetraose syrup containing at least 50% maltotetraose, d.s.b., commercialized by Hayashibara Shoji, Inc, Okayama, Japan, seven parts by weight of "TREHASTAR®", a trehalose syrup containing at least 28% trehalose, d.s.b., commercialized by Hayashibara Shoji, Inc., Okayama, Japan, five parts by weight of a coffee extract, 2.2 parts by weight of whole milk powder, one part by weight of skim milk, 0.04 part by weight of sucrose fatty acid ester, 0.06 part by weight of sodium bicarbonate, and 82 parts by weight of water were mixed in the usual manner to obtain a coffee beverage containing trehalose.

The product, having a satisfactory flavor and taste, is useful as a health food for maintaining/promoting the health conditions of the bone.

Example 5
Supplemental Health Food

Fifty-five parts by weight of "TREHAOSE®", a crystalline trehalose powder containing at least 98% trehalose, d.s.b., commercialized by Hayashibara Shoji, Inc, Okayama, Japan, 40.5 parts by weight of corn starch, and 2.5 parts by weight of crystalline cellulose were mixed. The mixture was in the usual manner kneaded while an adequate amount of water was dropping thereunto by spraying, subjected to fluidized-bed granulation, pulverized, and sized to obtain a powder for tabletting. Thereafter, the powder was admixed with two parts by weight of sucrose fatty acid ester as a brightener and tabletted by a tabletting machine, with a punch of 11 mm in diameter, to obtain tablets, about 300 mg/tablet.

The product, having a satisfactory swallowability and easy disintegrability in the intestinal tracts, is useful as a supplemental health food for maintaining/promoting the health conditions of the bone.

Example 6
Supplemental Health Food

Thirty-nine parts by wight of "TREHAOSE®", a food grade trehalose with a purity of at least 98% commercialized by Hayashibara Shoji, Inc., Okayama, Japan, 25 parts by weight of a powdered natural coral, nine parts by weight of a cattle bone meal, 12 parts by weight of powdered yoghurt, 10 parts by weight of guar gum, 1.9 parts by weight of vitamin C, and 0.1 part by weight of a glycosyl vitamin P were kneaded while water was dropping in the mixture by spraying. Then, the resulting mixture was subjected to fluidized-bed-granulation, pulverized, and sized to obtain a powder for tablets. The powder was mixed to homogeneity with three parts by weight of sugar fatty acid ester as a gloss agent, and tabletted with a tabletting machine with a punch of 6-mm in diameter into a tablet containing trehalose, about 200 mg weight.

The product supplemented with calcium is easily swallowable and can be arbitrarily used as a supplemental health food for maintaining and/or promoting the health.

Example 7
Injection

"TREHAOSE®", a food grade trehalose with a purity of at least 98% commercialized by Hayashibara Shoji, Inc., Okayama, Japan, which had been removed pyrogens using an ion exchanger and an activated charcoal in the usual manner, was dissolved by heating in distilled water for injection, which had been equilibrated with an adequate amount of 0.5 M phosphate buffer (pH 7.0), to give a 10 w/w % trehalose solution. The solution was filtered with a membrane filter having a pore size of 0.22 $\mu$m, and 200-ml aliquots of the filtrate were distributed to glass bottles.

Thereafter, the gas within the bottles was replaced with nitrogen gas, sealed, and sterilized using a high-pressure steam to obtain a colorless opaque solution with a transmittance of 99.9% at a wavelength of 430 nm.

The product with a satisfactory stability can be effectively used as an injection for treating/preventing osteoporosis.

Example 8
Dried Injection

"TREHAOSE®", a food grade trehalose with a purity of at least 98% commercialized by Hayashibara Shoji, Inc., Okayama, Japan, which had been removed pyrogens using an ion exchanger and an activated charcoal in the usual manner, was dissolved by heating in distilled water for injection, which had been equilibrated with an adequate amount of 0.5 M phosphate buffer (pH 7.0), to give a 10 w/w % trehalose solution. The solution was filtered with a membrane filter having a pore size of 0.22 $\mu$m, and 200-ml aliquots of the filtrate were distributed to glass bottles. Thereafter, the bottles, containing a colorless, opaque solution with a transmittance of 99.9% at a wavelength of 430 nm, were lyophilized, followed by replacing the inner gas within the bottles with nitrogen gas and sterilizing the bottles with a relatively-high pressure steam to obtain a dried injection.

The product is dissolved in an adequate amount of distilled water for injection before use. The product with a satisfactory stability can be effectively used as an injection for treating/preventing osteoporosis.

As described above, the present invention was made based on the finding that trehalose controls the osteogenesis, inclined to a negative equilibrium side, to the desired conditions, and then exerts an outstanding anti-osteoporosis action. Because of the action, the present agent comprising trehalose as an effective ingredient maintains and promotes the health conditions of the bone and prevents osteoporosis. When administered to patients with geriatric osteoporosis including postmenopausal osteoporosis; those with hyperthyroidism, hypogonadism, Cushing syndrome, osteogenesis imperfecta tarda, and homocysteinuria; those whose bones became to be easily fractured due to side effects of traumas and excessive administrations of steroid hormones; and those with abnormality in an estrogen receptor gene, the present agent relieves lumbago and arthralgia attendant on osteoporosis and increases the bone content to prevent fracture. Trehalose is a saccharide widely distributed in nature; it can be used daily with lesser side effects. Since the present agent inhibits the increase of low density lipoprotein (LDL) over the normal level in humans and mammals, the administration of trehalose to postmenopausal females exerts an satisfactory effect on the treatment/prevention of circulatory diseases including hemodynamic disorders, arteriosclerosis, thrombosis, myocardial infarction, and cerebral infarction, which are induced by an excessive amount of LDL.

While there has been described what is at present considered to be the preferred embodiments of the invention, it will be understood the various modifications may be made therein, and it is intended to cover in the appended claims all such modifications as fall within the true spirits and scope of the invention.

We claim:

1. A method for treating and/or preventing osteoporosis by administering an agent to humans and animals in need thereof, said agent comprising trehalose in an amount sufficient therefor as an effective ingredient.

2. The method according to claim 1, wherein said agent is administered to said humans and animals orally or parenterally.

3. The method according to claim 2, wherein said agent is administered to said humans and animals at a dose of about 0.5 to about 100 g/adult/day when administered orally.

4. The method according to claim 2, wherein said agent is and animals at a dose of about 0.5 to about 100 g/adult/day when administered parenterally.

5. A method for inhibiting the differentiation of osteoclasts by administering an agent to humans and animals in need thereof, said agent comprising trehalose in an amount sufficient therefor as an effective ingredient.

6. The method according to claim 5, wherein said agent is administered to said humans and animals orally or parenterally.

7. The method according to claim 6, wherein said agent is administered to said humans and animals at a dose of about 0.5 to about 100 g/adult/day when administered orally.

8. The method according to claim 6, wherein said agent is administered to said humans and animals at a dose of about 0.5 to about 100 g/adult/day when administered parenterally.

9. The method according to claim 1, wherein said agent further comprises another ingredient for ease of the administration of said trehalose.

10. The method according to claim 9, wherein said other ingredient is one or more ingredients selected from the group consisting of saccharides excluding trehalose, electrolytes, amino acids, vitamins, lipids, and mixtures thereof.

11. The method according to claim 1, wherein said agent contains at least 0.1 w/w % of said trehalose.

12. The method according to claim 1, wherein said agent is in the form of a food product or an injection for intravenous administration.

13. The method according to claim 5, wherein said agent further comprises another ingredient for ease of the administration of said trehalose.

14. The method according to claim 13, wherein said other ingredient is one or more ingredients selected from the group consisting of saccharides excluding trehalose, electrolytes, amino acids, vitamins, lipids, and mixtures thereof.

15. The method according to claim 5, wherein said agent contains at least 0.1 w/w % of said trehalose.

16. The method according to claim 5, wherein said agent is in the form of a food product or an injection for intravenous administration.

* * * * *